United States Patent
Kosover et al.

(10) Patent No.: US 8,013,083 B2
(45) Date of Patent: Sep. 6, 2011

(54) MEANS FOR CONTROLLING THE EXOTHERMIC REACTION OF STYRENIC MONOMERS WITH SULFONIC ACIDS

(75) Inventors: Vilan Kosover, Cheshire, CT (US);
Jesus A. Fabian, Wethersfield, CT (US);
Istvan Lippai, Naugatuck, CT (US);
Brigitte Benage, Wolcott, CT (US);
Gerald J. Abruscato, Southington, CT (US)

(73) Assignee: ChemTura Corporation, Middlebury, CT (US)

(*) Notice: Subject to any disclaimer, the term of this patent is extended or adjusted under 35 U.S.C. 154(b) by 872 days.

(21) Appl. No.: 11/345,194

(22) Filed: Jan. 31, 2006

(65) Prior Publication Data

US 2006/0178489 A1    Aug. 10, 2006

Related U.S. Application Data

(60) Provisional application No. 60/649,563, filed on Feb. 4, 2005.

(51) Int. Cl.
*C08F 2/38* (2006.01)
*C08F 12/02* (2006.01)

(52) U.S. Cl. ............... 526/82; 526/83; 526/84; 526/85; 526/346

(58) Field of Classification Search ............ 526/82, 526/83, 84, 85, 346
See application file for complete search history.

(56) References Cited

U.S. PATENT DOCUMENTS

| | | | |
|---|---|---|---|
| 2,522,680 A * | 9/1950 | Kropa et al. ................. 526/270 |
| 2,867,672 A | 1/1959 | Hemmerich ............... 260/666.5 |
| 3,148,225 A | 9/1964 | Albert |
| 4,053,304 A | 10/1977 | Tsuda |
| 4,086,147 A | 4/1978 | Watson ............................ 203/9 |
| 4,468,343 A | 8/1984 | Butler et al. .................. 252/403 |
| 4,654,450 A | 3/1987 | Miller ............................... 585/5 |
| 4,670,131 A * | 6/1987 | Ferrell ..................... 208/48 AA |
| 5,212,272 A * | 5/1993 | Sargent et al. ............. 526/317.1 |
| 5,254,760 A | 10/1993 | Winter et al. ..................... 585/5 |
| 5,290,888 A | 3/1994 | Gatechair et al. ............... 526/83 |
| 5,446,220 A * | 8/1995 | Arhancet .......................... 585/5 |
| 5,590,232 A | 12/1996 | Wentworth et al. |
| 5,648,573 A | 7/1997 | Arhancet et al. |
| 5,824,829 A | 10/1998 | Maeda et al. ..................... 585/3 |
| 5,922,244 A | 7/1999 | Koch et al. |
| 5,932,735 A | 8/1999 | Cunkle et al. ................. 546/242 |
| 6,136,951 A | 10/2000 | Benage et al. |
| 6,143,205 A | 11/2000 | Sutoris et al. ................. 252/405 |
| 6,156,858 A * | 12/2000 | Keoshkerian et al. ........ 526/204 |
| 6,653,414 B2 | 11/2003 | Benage et al. |
| 6,660,181 B2 | 12/2003 | Benage et al. |
| 6,685,823 B2 * | 2/2004 | Benage et al. ........... 208/48 AA |
| 7,045,647 B2 | 5/2006 | Benage |
| 7,473,795 B2 | 1/2009 | Benage |
| 2004/0147797 A1 | 7/2004 | Tanizaki et al. ............... 585/950 |

FOREIGN PATENT DOCUMENTS

| | | |
|---|---|---|
| EP | 0398633 A1 | 11/1990 |
| JP | 8034748 | 2/1996 |
| JP | 2004300307 A | 10/2004 |
| JP | 2004300385 | 10/2004 |
| WO | 2006036274 | 4/2006 |
| WO | WO2006036274 | 4/2006 |
| WO | 2006051941 | 5/2006 |

* cited by examiner

*Primary Examiner* — William Cheung
(74) *Attorney, Agent, or Firm* — Joseph Suhadolnik

(57) ABSTRACT

A method for inhibiting the premature polymerization of styrenic monomers is disclosed wherein the method comprises adding to said monomers a combination of:
(A) at least one inhibitor that is a sulfonic acid compound in a concentration sufficient to initiate cationic polymerization of said styrenic monomers at any point of the manufacturing or purification process and cause a resulting temperature increase; and
(B) at least one amine in a concentration sufficient to reduce said cationic polymerization and said temperature increase;

whereby an uncontrolled exothermic reaction between said sulfonic acid compound and said styrenic monomers will be prevented.

3 Claims, No Drawings

MEANS FOR CONTROLLING THE EXOTHERMIC REACTION OF STYRENIC MONOMERS WITH SULFONIC ACIDS

We claim the benefit under Title 35, United States Code, §120 of U.S. Provisional Application No. 60/649,563, filed Feb. 4, 2005, entitled MEANS FOR CONTROLLING THE EXOTHERMIC REACTION OF STYRENIC MONOMERS WITH SULFONIC ACIDS.

BACKGROUND OF THE INVENTION

1. Field of the Invention

The present invention is directed to an improvement in a method for the inhibition of the polymerization of styrenic monomers wherein the inhibitor comprises a sulfonic acid.

2. Description of Related Art

Many ethylenically unsaturated monomers undesirably polymerize at various stages of their manufacture, processing, handling, storage, and use. Polymerization, such as thermal polymerization, during their purification results in the loss of the monomer, i.e., a lower yield, and an increase in the viscosity of any tars that may be produced. The processing and handling of the higher viscosity tars then requires higher temperature and work (energy cost) to remove residual monomer.

Polymerization can also result in equipment fouling and losses in production efficiency owing to the deposition of polymer in or on the equipment being used. These deposits must be removed from time to time, leading to additional loss in production of the monomer.

A wide variety of compounds has been proposed and used for inhibiting uncontrolled and undesired polymerization of ethylenically unsaturated monomers. However, many of these compounds have not been fully satisfactory.

U.S. Pat. No. 2,867,672 discloses that the polymerization of uninhibited styrene condensing in liquid form on the surfaces containing the vapor space above the liquid level of the main body of styrene in a tank may be minimized, by spraying the surfaces enclosing the vapor space with a styrene polymerization inhibitor.

U.S. Pat. No. 4,086,147 discloses a process for the distillation of readily polymerizable vinyl aromatic compounds comprising subjecting a vinyl aromatic compound to elevated temperatures in a distillation system in the presence of a polymerization inhibitor comprising m-nitro-p-cresol.

U.S. Pat. No. 4,468,343 discloses a compound and a process for utilizing the compound to prevent the polymerization of vinyl aromatic compounds, such as styrene, during heating. The composition includes effective amounts of 2,6-dinitro-p-cresol and either a phenylenediamine or 4-tert-butylcatechol respectively, to act as a polymerization co-inhibitor system in the presence of oxygen.

U.S. Pat. No. 5,254,760 discloses the inhibition of the polymerization of a vinyl aromatic compound, such as styrene, during distillation or purification by the presence of at least one stable nitroxyl compound together with at least one aromatic nitro compound.

U.S. Pat. No. 5,290,888 discloses a process for stabilizing an ethylenically unsaturated monomer or oligomer from premature polymerization whereby a stabilizing amount of an N-hydroxy substituted hindered amine is added to said polymerizable monomer or oligomer. The ethylenically unsaturated monomer or oligomer encompasses vinyl monomers or oligomers bearing at least one polymerizable moiety. The N-hydroxy substituted hindered amine is said to inhibit premature polymerization in the liquid and/or vapor phase.

U.S. Pat. No. 5,446,220 discloses methods for inhibiting the polymerization of vinyl aromatic monomers in oxygen-free processing systems. These methods comprise adding from 1 to about 10,000 parts per million parts monomer of a combination of a dinitrophenol compound, a hydroxylamine compound and a phenylenediamine compound. Preferably, 2-sec-butyl-4,6-dinitrophenol or 4,6-dinitro-o-cresol are used in combination with bis-(hydroxypropyl)hydroxylamine and N,N'-di-sec-butyl-p-phenylenediamine.

U.S. Pat. No. 5,932,735 discloses that selected derivatives of 1-oxyl-2,2,6,6-tetramethyl-4-hydroxypiperidine are effective as inhibitors to prevent the premature polymerization of acrylic and methacrylic acids, their esters, their amides, vinyl acetate and acrylonitrile in the presence of water.

U.S. Pat. No. 6,143,205 discloses a mixture for inhibiting the premature polymerization of monomers that contains (A) vinyl-containing monomers, and (B) an effective amount of a mixture of (I) from 0.05 to 4.5% by weight, based on the total mixture (B), of at least one N-oxyl compound of a secondary amine which carries no hydrogen atoms on the .alpha.-carbon atoms and (ii) from 99.95 to 95.5% by weight, based on the total mixture (B), of at least one nitro compound.

U.S. Published Application No. 2004/0147797 discloses a process for inhibiting the polymerization of an aromatic vinyl compound which is capable of efficiently inhibiting the polymerization of an aromatic vinyl compound not only in an initial stage but also over a long term in the stage of producing, purifying, storing or transporting the aromatic vinyl compound, and which is said to be excellent in handling. The process comprises adding 2-nitrophenol compound in combination with a sulfonic acid compound to the aromatic vinyl monomer during the stage of producing, purifying, storing or transporting the aromatic vinyl compound.

The foregoing are incorporated herein by reference in their entirety.

SUMMARY OF THE INVENTION

As noted above, it is known in the art to inhibit the polymerization of styrene monomer by the addition thereto of a sulfonic acid in combination with a 2-nitrophenol. However, styrene monomer is known to react with sulfonic acids, e.g., a benzenesulfonic acid compound, giving rise to a cationically initiated polymerization accompanied by a significant temperature increase. This exothermic reaction takes place even at very low sulfonic acid concentrations (below one percent by weight of sulfonic acid, based on the weight of the styrene). The reaction occurs at temperatures from about 25° C. to 130° C. and the final product is a brown viscous liquid. It has now been discovered that by means of the addition of an amine this cationically initiated polymerization and consequent uncontrolled exothermic reaction will not take place.

Thus, the present invention is directed to a method for inhibiting the premature polymerization of styrenic monomers comprising adding to said monomers a combination of:

(A) at least one inhibitor that is a sulfonic acid compound in a concentration sufficient to initiate cationic polymerization of said styrenic monomers at any point of the manufacturing or purification process and cause a resulting temperature increase; and (B) at least one amine in a concentration sufficient to reduce said cationic polymerization and said temperature increase;

whereby an uncontrolled exothermic reaction between said sulfonic acid compound and said styrenic monomers will be prevented.

In another aspect, the present invention is directed to a composition comprising:

(A) a styrenic monomer;

(B) at least one inhibitor that is a sulfonic acid compound in a concentration sufficient to initiate cationic polymerization of the styrenic monomer at any point of the manufacturing or purification process and cause a resulting temperature increase; and (C) at least one amine in a concentration sufficient to reduce said cationic polymerization and said temperature increase.

In a preferred embodiment, the inhibitor comprises one or more inhibiting species in addition to the sulfonic acid compound.

DESCRIPTION OF THE PREFERRED EMBODIMENTS

As stated above, the present invention is directed to a method for inhibiting the premature polymerization of styrenic monomers comprising adding to said monomers a combination of:

(A) at least one inhibitor that is a sulfonic acid compound in a concentration sufficient to initiate cationic polymerization of said styrenic monomers at any point of the manufacturing or purification process and cause a resulting temperature increase; and (B) at least one amine in a concentration sufficient to reduce said cationic polymerization and said temperature increase;

whereby an uncontrolled exothermic reaction between said sulfonic acid compound and said styrenic monomers will be prevented.

Also as noted above, additional inhibitors can, if desired, be present, such as nitrophenols, nitroxyl compounds, nitrosoanilines, and the like.

The sulfonic acid compounds that can be employed in the practice of the present invention include, but are not limited to, those described in U.S. Published Application No. 2004/0147797, i.e., compounds of the structure:

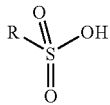

wherein R represents a hydroxyl group, a straight or branched chain alkyl group having from 1 to about 32 carbon atoms, an alkylphenyl or an alkylnaphthyl group each having at least one straight or branched chain alkyl group having 1-32 carbon atoms, for example, sulfuric acid, toluenesulfonic acid, xylenesulfonic acid, cumenesulfonic acid, dodecylbenzenesulfonic acid, pentadecylbenzenesulfonic acid, dinonylnaphthalenesulfonic acid, and the like.

Preferably, R is an alkylphenyl group having at least one straight chain or branched chain alkyl of from 1 to 18 carbon atoms including, but not limited to, methyl, ethyl, propyl, butyl, pentyl, hexyl, heptyl, octyl, 2-ethyl hexyl, nonyl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, tetracosyl, pentacosyl, triacontyl, isomers of the foregoing, and the like; or cyclic alkyl groups, such as cyclopentyl, cyclohexyl, cycloheptyl, cyclooctyl, and cyclododecyl.

In the practice of the present invention, the sulfonic acid compound inhibitors are present in a concentration sufficient to initiate cationic polymerization of said styrenic monomers at any point of the manufacturing or purification process and cause a resulting temperature increase. In a preferred embodiment, the sulfonic acid compound inhibitors are present in a concentration in the range of from about 0.001 to about 10 percent by weight in the monomer, more preferably of from about 0.5% to about 3 percent by weight.

Another feature of the method of the present invention is the presence of at least one amine in a concentration sufficient to reduce the cationic polymerization of the styrenic monomers and the resulting temperature increase referred to above. In a preferred embodiment, the amine will be present in an amount in the range of from about 0.1 to about 2.0 molar equivalents per molar equivalent of the sulfonic acid compound, more preferably, from about 0.5 to about 1.0 molar equivalents per molar equivalent of the sulfonic acid compound.

Such amines can be primary, secondary, or tertiary and can be alkyl, aryl, alkaryl, or aralkyl. More than one amine moiety can be present on a given amine compound. Such amines include, but are not limited to, triethyl amine, diethylamine, tributylamine, pyridine, 2,6-dimethyl-4-aminopyridine, 2,6-lutidine, N-(1,4-dimethylpentyl)aniline, N-methyl pyrrolidinone (NMP), α-naphthylamine, thiodiarylamines, p-phenylenediamine, o-phenylenediamine, 2,4-diamino diphenylamine, cyclohexyl naphthyl amine, polybutyl amines, methyl aniline, diphenyl-p-phenylene diamine, phenyl-β-naphthylamine, isopropoxydiphenylamine, aldol-α-naphthyl amine, symmetrical di-β-naphthyl-p-phenylenediamine, trimethyl dihydroquinoline, ditolylamines, phenyl-α-naphthylamine, phenyl-β-naphthylamine, diaminophenol, 4-cyclohexylaminophenol, p-aminophenol, o-aminophenol, 5-amino-2-hydroxytoluene, and the like. The preferred amines for use in the practice of the present invention are 4triethyl amine, diethylamine, tributylamine, pyridine, N-(1, 4-dimethylpentyl)aniline, and N-methyl pyrrolidone.

Where nitrophenols are also employed in the practice of the present invention, they can include, but are not limited to, 2,6-dinitro-4-methylphenol, 2-nitro-4-methylphenol, 2,4-dinitro-1-naphthol, 2,4,6-trinitrophenol (picric acid), 2,4-dinitro-6-methylphenol, 2,4-dinitrophenol, 2,4-dinitro-6-sec-butylphenol, 2,6-dinitro-4-sec-butylphenol, 4-cyano-2-nitrophenol, 3-iodo-4-cyano-5-nitrophenol, m-nitro-p-cresol, 2,6-dinitro-p-cresol, and the like. 2,4-Dinitro-6-sec-butylphenol is preferred.

Where the inhibiting system of the present invention comprises an additional inhibitor that is a nitrosoaniline, it can be an N-nitrosoaniline, such as p-nitroso dimethyl aniline, or a C-nitrosoaniline. Preferably, the nitrosoaniline compound is a C-nitrosoaniline.

C-nitrosoaniline compounds can be prepared by C-nitrosation of the corresponding anilines in any typical manner used for the C-nitrosation of aromatic amines. For example, reaction of the amine with cold nitrous acid produces an N-nitroso compound that rearranges to a para-nitrosoaniline under the influence of an excess of hydrochloric acid. In some cases, it is more convenient to effect the nitrosation and rearrangement in one step by conducting the reaction in methanol solution in the presence of an excess of hydrogen chloride under anhydrous conditions. This procedure is described in U.S. Pat. No. 2,046,356.

Those skilled in the art will be aware that nitrosoaniline derivatives are understood to tautomerize to quinone imineoxime derivatives, i.e.,

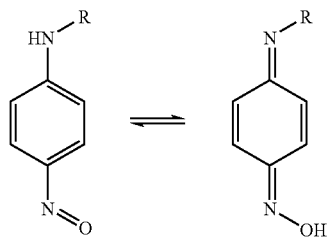

See, for example, Sidgwick, N. V., *The Organic Chemistry of Nitrogen*, Third Edition, Clarendon Press, Oxford, 1966. Thus, both forms can be present, especially in solution at elevated temperatures, and can be expected to contribute to the inhibiting activity of these compounds.

The nitrosoanilines that can be employed in the practice of the present invention are preferably of the structure:

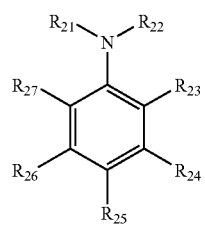

wherein $R_{21}$, and $R_{22}$ are independently selected from the group consisting of hydrogen, alkyl, aryl, acyl, hydroxyl, alkoxy, nitroso, and sulfonyl, or $R_{21}$ and $R_{22}$ can form a cyclic ring that is aryl, cycloalkyl, polyaryl, or heterocyclic;
$R_{23}$ through $R_{27}$ are independently selected from the group consisting of hydrogen, alkyl, aryl, acyl, hydroxyl, alkoxy, acyloxy, $NR_{28}(R_{29})$, nitro, nitroso, halogen, and sulfonyl, or any two adjacent R's can form a cyclic ring that is aryl, cycloalkyl, polyaryl, or heterocyclic, provided that at least one of $R_{23}$ through $R_{27}$ must be a nitroso group; and
$R_{28}$ and $R_{29}$ are independently selected from the group consisting of hydrogen, alkyl, aryl, acyl, and nitroso. Preferably $R_{28}$ is hydrogen and $R_{29}$ is alkyl.

The styrenic monomer, the premature polymerization and polymer growth of which is an object of the present invention, can be any such monomer for which unintended polymerization and/or polymer growth during its manufacture, storage, and/or distribution is a problem. Among those monomers that will benefit from the practice of the present invention are: styrene, α-methylstyrene, styrene sulfonic acid, vinyltoluene, divinylbenzenes, polyvinylbenzenes, alkylated styrene, 2-vinylpyridine, and the like.

Those skilled in the art will understand that, if desired, free radical scavengers can also be included in the practice of the present invention. For example, air or $O_2$, as disclosed in U.S. Pat. Nos. 5,545,782 and 5,545,786, can be added, as can the aromatic nitro compounds disclosed in U.S. Pat. No. 5,254,760, the dihetero-substituted benzene compounds having at least one transferable hydrogen, e.g., a quinone derivative such as the mono-methyl-ether of hydroquinone disclosed in European Patent Application 0 765 856 A1, the iron compounds disclosed in WO 98/25872, and other inhibitors, e.g., phenolics and certain inorganic salts, well-known to those skilled in the art.

The polymerization inhibitor(s) and the amine(s) can be introduced into the monomer to be protected by any conventional method. They can, for example, be added as a concentrated solution in suitable solvents just upstream from the point of desired application by any suitable means. In addition, individual inhibiting components can be injected separately into the distillation train along with the incoming feed and/or through separate and multiple entry points, provided there is an efficient distribution of the inhibiting composition. Since the inhibitors are gradually depleted during the distillation operation, it is generally advantageous to maintain the appropriate amount of them in the distillation apparatus by adding them during the course of the distillation process. Adding inhibitors can be done either on a generally continuous basis or intermittently, in order to maintain the inhibitor concentration above the minimum required level.

The advantages and the important features of the present invention will be more apparent from the following examples.

EXAMPLES

Example 1

In a 250 mL round-bottomed flask, equipped with a reflux condenser and thermometer, were placed one gram of boiling chips, 95 grams of styrene monomer, and five grams of dodecylbenzenesulfonic acid. The reaction mixture was then heated by immersing in a 135° C. oil bath and the temperature was carefully monitored. As soon as the temperature of reaction mixture reached 80-90° C., the heat source (oil bath) was removed and the temperature rose to 200° C. in about one minute. The resulting dark viscous mixture was then allowed to cool at room temperature.

Example 2

In a 250 mL round-bottomed flask, equipped with a reflux condenser and thermometer, were placed one gram of boiling chips, 130 grams of styrene monomer, 7.5 grams of dodecylbenzenesulfonic acid, and 2.5 grams of NMP. The reaction mixture was then heated by immersing in a 135° C. oil bath and the temperature was carefully monitored. The temperature increased to 120° C. and stayed there for 5 minutes with no further increase.

Examples 3-5

The prevention of the exothermic reaction was also tested using structurally different amines. In these experiments, a two gram sample was immersed in a room temperature oil bath and heated to 135° C. The samples contained 3.5% dodecylbenzenesulfonic acid (DDBSA), 1% 2,4-dinitro-6-sec-butylphenol (DNBP), and amine at 1:1 DDBSA:amine molar equivalent ratio in styrene monomer. Triethylamine, pyridine, and N-(1,4-dimethylpentyl)aniline were found to protect against the exothermic reaction because in their presence no temperature increase was observed.

Examples 6-8

In addition to knowing the effect of amines to prevent the exothermic reaction, the objective of the next experiments was to estimate the minimum level of the dodecylbenzenesulfonic acid to become reactive exothermically with styrene monomer.

Three samples were prepared containing 3.5, 1.5, and 0.5% dodecylbenzenesulfonic acid in styrene monomer and the samples were studied using Differential Scanning Calorimetry (DSC). The samples also contained 1% DNBP. The results are as follows:

3.5% DDBSA in styrene monomer (SM), exothermic reaction starts at 88° C.

1.5% DDBSA in SM, exothermic reaction starts at 99° C.

0.5% DDBSA in SM, a mild exothermic reaction starts at 104° C.

Therefore, an exothermic reaction, measurable by these laboratory test methods, takes place when the amount of DDBSA is approximately 0.5% or higher.

It is important to note that in the manufacture of styrene monomer the levels of inhibitors could reach 0.5% or higher, and that having such a level without amine protection could be dangerous. Furthermore, in the styrene manufacturing process, the magnitude of the temperature rise could be greater because, unlike in the above laboratory tests, the generated heat cannot dissipate owing to the large volume of materials.

Examples 9-11

The next set of experiments was designed to estimate the amount of amine necessary to prevent the exothermic reaction of sulfonic acid and styrene. Three samples were prepared containing 3.5% dodecylbenzenesulfonic acid, 1% DNBP, and the indicated molar equivalents of NMP. The exothermic characteristics of samples were studied using DSC with the following results:

0.1 molar equivalent NMP, exothermic reaction starts at 92° C.

0.25 molar equivalent NMP; exothermic reaction starts at 95° C.

0.5 molar equivalent NMP, no exothermic reaction is observed.

Therefore, in the case of NMP under these conditions, the required minimum quantity of amine to protect against the exothermic reaction is between 0.25 and 0.5 molar equivalent per molar equivalent of dodecylbenzenesulfonic acid.

In view of the many changes and modifications that can be made without departing from principles underlying the invention, reference should be made to the appended claims for an understanding of the scope of the protection to be afforded the invention.

What is claimed is:

1. A method for inhibiting the premature polymerization of styrenic monomers comprising adding to said monomers a combination of:

(A) from about 0.5 percent by weight to about 3 percent by weight of at least one sulfonic acid compound selected from the group consisting of toluenesulfonic acid, xylenesulfonic acid, cumenesulfonic acid, dodecylbenzenesulfonic acid, pentadecylbenzenesulfonic acid, dinonylnaphthalenesulfonic acid; and (B) about 0.25 to about 0.5 molar equivalents per molar equivalent of said sulfonic acid compound of at least one amine selected from the group consisting of pyridine, 2,6-dimethyl-4-aminopyridine, 2,6-lutidine, N-(1,4-dimethylpentyl)aniline, and methyl aniline; and, (C) at least one inhibitor selected from the group consisting of a nitrophenol, a nitroxyl compound, and a nitrosoaniline whereby an uncontrolled exothermic reaction of styrenic monomer will be prevented.

2. The method of claim 1 wherein said inhibitor (C) is 2,4-dinitro-6-sec-butylphenol.

3. The method of claim 1 wherein said inhibitor (C) is a nitrosoaniline of the structure:

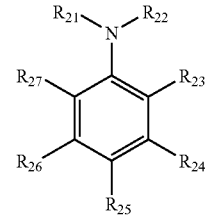

wherein $R_{21}$ and $R_{22}$ are independently selected from the group consisting of hydrogen, alkyl, aryl, acyl, hydroxyl, alkoxy, nitroso, and sulfonyl, or $R_{21}$ and $R_{22}$ can form a cyclic ring that is aryl, cycloalkyl, polyaryl, or heterocyclic;

$R_{23}$ through $R_{27}$ are independently selected from the group consisting of hydrogen, alkyl, aryl, acyl, hydroxyl, alkoxy, acyloxy, $NR_{28}(R_{29})$, nitro, nitroso, halogen, and sulfonyl, or any two adjacent R's can form a cyclic ring that is aryl, cycloalkyl, polyaryl, or heterocyclic, provided that at least one of $R_{23}$ through $R_{27}$ must be a nitroso group; and $R_{28}$ and $R_{29}$ are independently selected from the group consisting of hydrogen, alkyl, aryl, acyl, and nitroso.

* * * * *